United States Patent [19]

Karin et al.

[11] Patent Number: 5,776,689
[45] Date of Patent: Jul. 7, 1998

[54] PROTEIN RECRUITMENT SYSTEM

[75] Inventors: Michael Karin, San Diego, Calif.; Stephen J. Elledge, Houston, Tex.; Ami Aronheim, San Diego, Calif.

[73] Assignees: The Regents of the University of California, Oakland, Calif.; Baylor College of Medicine, Houston, Tex.

[21] Appl. No.: 683,877

[22] Filed: Jul. 19, 1996

[51] Int. Cl.$^6$ .................. C12Q 1/68; C12N 15/81; C12N 15/63; C12N 21/04

[52] U.S. Cl. .................. 435/6; 435/254.21; 435/320; 435/325; 536/23.4

[58] Field of Search ............... 435/6, 69.1, 91.1, 435/240.1, 320.1, 254.2; 536/23.4

[56] References Cited

U.S. PATENT DOCUMENTS 5,283,173  2/1994  Fields et al. ................... 435/6

FOREIGN PATENT DOCUMENTS

WO96/02561 A1  2/1996  WIPO ............... C07H 21/04

OTHER PUBLICATIONS

Spencer et. al., A general strategy for producing conditional alleles of Src–like tyrosine kinases. PNAS. USA. vol. 92:9505–9809, Oct. 1995.

Chardin, Pierre et al., "Human Sos1: A Guanine Nucleotide Exchange Factor for Ras that Binds to GRB2," *Science* 260:1338–1343 (1993).

Quilliam, Lawrence A. et al., "Membrane–targeting Potentiates Guanine Nucleotide Exchange Factor CDC25 and SOS1 Activation of Ras Transforming Activity," *Proc. Natl. Acad. Sci. USA.* 91:8512–8516 (1994).

Osborne, Mark A. et al., "The Yeast Tribrid System–Genetic Detection of Trans-Phosphorylated ITAM–SH2–Interactions," *Bio/tech.* 13:1474–1478 (1995).

Aronheim, Ami et al., "Membrane Targeting of the Nucleotide Exchange Factor Sos is Sufficient for Activating the Ras Signaling Pathway," *Cell.* 78:949–961 (1994).

*Primary Examiner*—Nancy Degen
*Assistant Examiner*—William Sandals
*Attorney, Agent, or Firm*—Campbell & Flores LLP

[57] ABSTRACT

The present invention provides a protein recruitment system, in which a protein-protein interaction is detected by the recruitment of an effector protein to a specific cell compartment, where the effector protein can activate a reporter molecule, provided that the effector protein is not a transcription factor. The invention also provides a drug screening assay using the protein recruitment system. In addition, the invention provides a kit for performing the protein recruitment system.

13 Claims, 2 Drawing Sheets

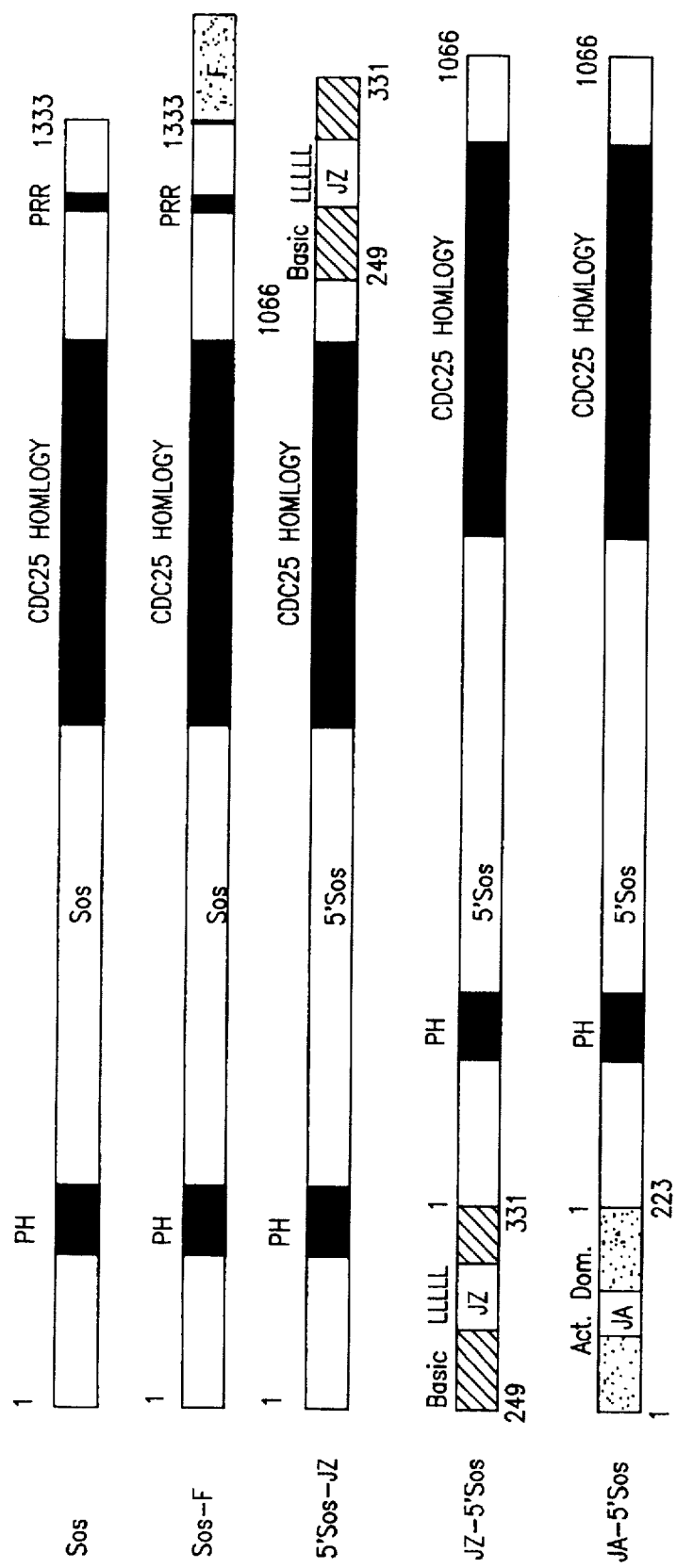
FIG. IA

5,776,689

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Lys Leu Asn Pro Pro Asp Glu Ser Gly Pro Gly Cys Met Ser Cys Lys
 1               5                  10                  15

Cys Val Leu Ser
            20
```

( 2 ) INFORMATION FOR SEQ ID NO:2:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
Ser Lys Asp Gly Lys Lys Lys Lys Lys Lys Ser Lys Thr Lys Cys Val
 1               5                  10                  15

Ile Met
```

( 2 ) INFORMATION FOR SEQ ID NO:3:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

```
Met Gly Ser Ser Lys Ser Lys Pro Lys Asp Pro Ser Gln Arg
```

( 2 ) INFORMATION FOR SEQ ID NO:4:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

CGGGATCCTC AAAATGTTTG CAACTG         26

( 2 ) INFORMATION FOR SEQ ID NO:5:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

CGGGATCCAG TCCCAGGAGC GGATC         25

( 2 ) INFORMATION FOR SEQ ID NO:6:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

GATCCCAAGC TTACCATGGG ATCCATGACT GCAAAGATGG AA         42

( 2 ) INFORMATION FOR SEQ ID NO:7:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

GAAGATCTTC ACCCGGGCAG CCGCGGGTGC TGCAC         35

( 2 ) INFORMATION FOR SEQ ID NO:8:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

GCGCCATGGA AGGATCCTCT CCAGAAGAAG AAGAG         35

( 2 ) INFORMATION FOR SEQ ID NO:9:

(i) SEQUENCE CHARACTERISTICS:
  (A) LENGTH: 35 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:9:

GAAGATCTTC ACCCGGGCAG CCGCGGGTGC TGCAC     35

(2) INFORMATION FOR SEQ ID NO:10:

(i) SEQUENCE CHARACTERISTICS:
  (A) LENGTH: 33 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:10:

GATCCCAAGC TTACCATGGA TTTCCTTTTG CCC     33

(2) INFORMATION FOR SEQ ID NO:11:

(i) SEQUENCE CHARACTERISTICS:
  (A) LENGTH: 32 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:11:

GAAGATCTCC CGGGTTTTCT TCGAAATTCA TT     32

(2) INFORMATION FOR SEQ ID NO:12:

(i) SEQUENCE CHARACTERISTICS:
  (A) LENGTH: 29 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:12:

CGGGATCCTC AATCATCTTC CACCAGTGA     29

(2) INFORMATION FOR SEQ ID NO:13:

(i) SEQUENCE CHARACTERISTICS:
  (A) LENGTH: 23 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:13:

CGGGATCCAA ATACCAACAG GAT     23

PROTEIN RECRUITMENT SYSTEM

This invention was made with government support under grant number PO1 CA50528 awarded by the National Cancer Institute. The government has certain rights in the invention.

BACKGROUND OF THE INVENTION

2. Field of the Invention

The present invention relates generally to molecular biology and more specifically to a method of identifying a protein involved in a protein-protein interaction.

1. Background Information

Regulation of growth and development of an individual and maintenance of a healthy state depend, in part, on the precise regulation of gene expression in response to various stimuli. Although gene expression occurs in the nucleus of a cell, the stimulus leading to the induction or repression of gene expression often occurs external to the cell. For example, a stimulus such as a growth factor may be elicited by one particular cell type in the body and may exert its growth promoting effect on a second cell type by binding to a specific receptor on the surface of the second cell type. Following binding to the receptor, the growth promoting signal is transduced into the cell, through a signal transduction pathway to the nucleus, resulting in the induction or repression of gene transcription.

Signal transduction pathways depend, in general, on one or more protein-protein interactions such that a signal generated, for example, outside of a cell is transduced into the cell, to the nucleus. Some of the best characterized signal transduction systems involve the signal initiated by the binding of a growth factor such as the epidermal growth factor to its specific cell surface receptor. Upon binding of a growth factor to the extracellular domain of the growth factor receptor, a signal is transmitted to the intracellular domain of the receptor. A series of protein-protein interactions results in activation of a signaling cascade from the cell surface to the cell nucleus.

A defect in any of the proteins involved in a signal transduction pathway can have deleterious effects on a cell. For example, mutant Ras proteins, which are a family of proteins involved in various signal transduction pathways, have been identified in a number of different types of cancers. This observation suggests that mutant Ras proteins mediate aberrant signal transduction, which can result, in part, in the unregulated cell growth associated with cancer. Similarly, mutations in other proteins, including, for example, oncogene products, that are involved in a signal transduction pathway can play a role in the development of a cancer or other metabolic or congenital disease.

In addition to mediating signal transduction, protein-protein interactions are involved in virtually all metabolic pathways that occur in a cell, including, for example, in the formation of holoenzyme complexes and in enzyme-substrate interactions. Furthermore, protein-protein interactions are involved in virus recognition of a particular cell type and in antibody recognition of a particular antigen.

Since protein-protein interactions are central to normal growth and development of the individual, the identification of the proteins involved in such interactions can provide insight into the normal cellular metabolism in an organism. More practically, the identification and characterization of particular protein-protein interactions permits the identification of defects in such interactions that are associated with a diseased state. The identification of such defects provides a target for potential therapies to cure or ameliorate the disease. In addition, the identification and characterization of protein-protein interactions provides a means to screen for drugs that alter the interaction. Such drugs can be useful, for example, to treat a disease caused, at least in part, by an aberrant protein-protein interaction.

Historically, proteins involved in a protein-protein interaction were identified by detecting the activity of the protein in a cell or in a bodily fluid, then the protein was purified using biochemical methods. Such methods of isolation, however, can be tedious, particularly if the protein is expressed at a low level or if only a few cells express the protein. Subsequently, immobilization of proteins to membrane filters led to the development of filter based assays using cDNA molecules expressed, for example, from phage. Again, however, these procedures were tedious.

More recently, a genetic method of identifying protein-protein interactions was developed. This method, known as the two hybrid assay, identifies the presence of a protein-protein interaction by detecting transcription of a reporter gene. This genetic method of identifying protein-protein interactions provides a significant advantage over the traditional biochemical methods of protein purification in that it provides a ready means to obtain the nucleic acid molecule encoding a particular protein. However, while the two hybrid assay provides a powerful method of identifying proteins involved in protein-protein interactions, the method is limited in the types of proteins that can be identified. For example, certain proteins are toxic to cells when expressed in the nucleus and, therefore, cannot be examined using the two hybrid assay. In addition, other proteins gratuitously contain domains that can activate transcription, resulting in false positive readouts using the two hybrid system. Thus, a need exists for other methods to identify gene products involved in protein-protein interactions. The present invention satisfies this need and provides related advantages as well.

SUMMARY OF THE INVENTION

The present invention provides a protein recruitment system, which is a method of detecting a protein-protein interaction by the recruitment of an effector protein, which is not a transcription factor, to a particular cell compartment, where the effector protein can activate a reporter molecule. The protein recruitment system is exemplified by a protein-protein interaction that results in recruitment of a guanine nucleotide exchange factor to the plasma membrane, where it effects the activation of a Ras reporter molecule.

The invention further provides a drug screening assay useful for identifying a drug that can alter a particular protein-protein interaction. In addition, the invention provides a kit useful for performing the protein recruitment system.

BRIEF DESCRIPTION OF THE DRAWING

FIGS. 1A and 1B provide schematic representations of the guanine nucleotide exchange factor, human Sos, and the various fusion proteins used in the exemplified protein recruitment system. Numbers above each construct indicate the amino acid positions of human Sos1 (hSos; Chardin et al., Science 260:1338–1343 (1993), which is incorporated herein by reference). Numbers below each construct indicate the amino acid positions of c-Jun, c-Fos, p110β or p85, as indicated.

Figure 1B:
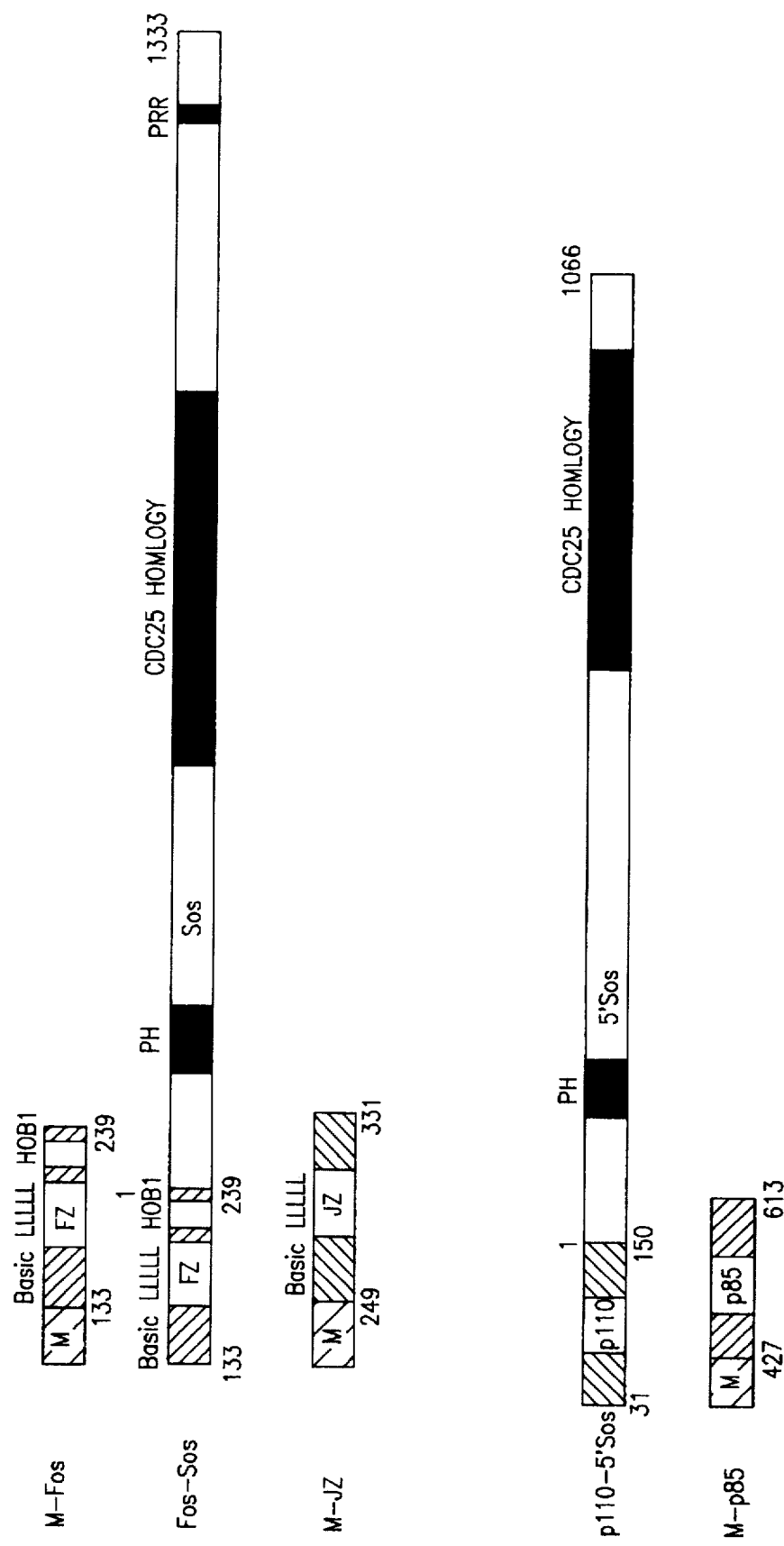

Abbreviations shown above each construct are as follows: "PH" is pleckstrin homology, "CDC25 HOMOLOGY" is the Sos catalytic pocket, "PRR" is proline rich region, "F" is farnesylation signal, "M" is myristoylation signal, "SOS" is son of sevenless, "Basic" is the basic regions of c-Jun and c-Fos, "LLLLL" is leucine zipper, and "HOB1" is c-Fos homology box-1. Abbreviations within each construct indicate that component of the fusion protein, except that the first construct, which represents the full length Sos, is not a fusion protein.

DETAILED DESCRIPTION OF THE INVENTION

The present invention provides a protein recruitment system, in which a protein-protein interaction is detected in a cell by the recruitment of an effector protein, which is not a transcription factor, to a specific cell compartment. Upon translocation of the effector protein to the cell compartment, the effector protein activates a reporter molecule present in that compartment, wherein activation of the reporter molecule is detectable, for example, by cell viability, indicating the presence of a protein-protein interaction.

As used herein, the term "protein recruitment system" means a cell based assay whereby a protein-protein interaction is identified due to recruitment of an effector protein to a specific cell compartment such that the effector protein can activate a reporter molecule. In addition, the term "protein-protein interaction" is used to mean that two or more proteins bind to each other relatively specifically such that the proteins associate in a cell.

The protein recruitment system is exemplified herein using yeast cell based assay, in which a protein-protein interaction results in the recruitment of a guanine nucleotide exchange factor (GEF) to the plasma membrane, where the GEF activates a Ras reporter molecule, resulting in the survival of cells that otherwise would not survive under the particular cell culture conditions. In view of the exemplified embodiment of the invention and the present disclosure, it will be recognized that the protein recruitment system can be practiced in essentially any type of cell, including, for example, mammalian, avian, insect and bacterial cells, and using various effector protein/reporter molecule systems.

Activation of a Ras protein is central to various signal transduction pathways. The members of the Ras superfamily of proteins are characterized, in part, by having GTPase activity. The Ras superfamily is classified into at least six families, including Ras (H-ras, N-ras K-rasA and K-rasB), Rho, Rab, Ran, Rad and Arf (see Quilliam et al., *BioEssays* 17:395–404 (1995)).

Activation of Ras is controlled by the guanine nucleotide exchange factors (GEFs), which convert inactive Ras-GDP to activated Ras-GTP. For example, exposure of an epithelial cell to epidermal growth factor (EGF) results in a growth promoting signal characterized by specific gene expression. EGF induces specific gene expression by binding to an EGF receptor expressed on the surface of cells that are programmed to respond to EGF. The EGF receptor is a transmembrane receptor consisting of an extracellular domain, which binds EGF, and an intracellular domain, which transmits the signal that EGF has bound to the receptor into the cell.

In resting cells, a GEF such as Sos is present in the cytoplasm in a complex with the adaptor protein, Grb2 (Buday and Downward, *Cell* 73:611–620 (1993)). Grb2 is a member of a family of proteins characterized by having domains that are homologous to Src. These domains are designated Src homology domains 2 and 3 (SH2 and SH3, respectively; see, for example, Schlessinger, *Curr. Opin. Genet. Devel.* 4:25–30 (1994)). Activation of a growth factor receptor due, for example, to binding by its cognate growth factor, results in autophosphorylation of the intracellular domain of the receptor on a particular tyrosine residue. Grb2 then can bind to the phosphorylated receptor through its SH2 domain, thereby effectively translocating Sos to the plasma membrane, where it can activate Ras by converting Ras-GDP to Ras-GTP (Buday and Downward, supra, 1993).

Ras generally is present in a cell in an inactive form containing bound GDP (Ras-GDP). Translocation of Sos to the plasma membrane allows Sos to interact with Ras such that Sos can effect conversion of Ras-GDP to Ras-GTP, thereby activating Ras. Among its other functions, activation of Ras results in translocation of Raf-1 to the plasma membrane, leading to Raf-1 activation. Raf-1 then can phosphorylate and activate the MEK proteins, which, in turn, activate the MAP kinases. These various activated proteins have numerous functions, including the ability to activate one or more transcription factors, resulting in transcription of specific genes (see Quilliam et al., supra, 1995).

A critical step in the activation of a Ras protein is the translocation of a GEF such as Sos to the plasma membrane. (Aronheim et al., *Cell* 78:949–961 (1994); Quilliam et al., *Proc. Natl. Acad. Sci., USA* 91:8512–8516 (1994), each of which is incorporated herein by reference). Numerous GEFs have been identified, including the *Saccharomyces cerevesiae* Cdc25 gene product. Based on information about Cdc25, GEFs were isolated from *S. pombe* (Ste6), Drosophila (DrSos) and various mammalian organisms (see, for example, Chardin et al., supra, 1993; see, also, Boguski and McCormick, *Nature* 366:643654 (1993); Shou et al., *Nature* 358:351–354 (1992); Martegani et al., *EMBO J.* 11:2151–2157 (1992); Wei et al., *Proc. Natl. Acad. Sci., USA* 89:7100–7104 (1992), each of which is incorporated herein by reference).

In mammalian cells, some GEFs are ubiquitously expressed in various different cell types, whereas others are expressed only in specific cell types. For example, the mammalian GEFs known as $Cdc25^{Mm}$ (or GRF) and Vav are expressed exclusively in brain and in hematopoeitic cells, respectively, whereas the mammalian GEF's known as Sos1, Sos2 and C3G are expressed in various cell types. Unless indicated otherwise, for convenience of discussion, the term "GEF" is used herein generically to mean any guanine nucleotide exchange factor, the term "Cdc25" and variations thereof such as "cdc25-2" are used to a refer to yeast GEFs, and the term "Sos" is used to mean a mammalian GEF.

The various GEFs share regions of structural similarity. In particular, the GEFs that activate Ras each contain a domain that is homologous to a region of Cdc25 and confers the guanine nucleotide exchange activity of the GEF (see Quilliam et al., supra, 1995; see, also, Lai et al, *Mol. Cell. Biol.* 13:1345–1352 (1993), which is incorporated herein by reference). Due, in part, to this conserved homology, a Ras GEF such as a mammalian GEF can activate, for example, the yeast Ras protein.

The requirement of GEF localization to the plasma membrane in order to effect Ras activation was demonstrated using mutant *S. cerevesiae* cdc25-2 cells, which express a temperature sensitive Cdc25 gene product (Petitjean et al., *Genetics* 124:797–806 (1990), which is incorporated herein by reference). A nucleic acid molecule encoding a C-terminal truncated human Sos (hSos), which lacked the Grb2 binding domain, was operably linked to a nucleic acid molecule encoding a farnesylation signal, which directs plasma membrane localization, and was expressed in the cdc25-2 cells. Expression of the membrane localizing hSos protein fully suppressed the growth deficiency of cdc25-2 mutants at 36° C., a temperature at which they normally undergo G1 arrest due to an inability to activate Ras (Aronheim et al., *Cell* 78:949–961 (1994), which is incorporated herein by reference).

Membrane localization of Sos also activated Ras in mammalian cells. Activation of Ras is known to induce transformation of NIH 3T3 cells. When membrane localizing Sos proteins were expressed in NIH 3T3 cells and transformation was scored, NIH 3T3 cells expressing the membrane localized Sos showed a transformed morphology similar to that of cells transformed by an oncogenic Ras protein (Aronheim et al., supra, 1994;

Quilliam et al., supra, 1994). These results demonstrated that direct recruitment of Sos to the plasma membrane was sufficient to activate Ras in yeast cells and in mammalian cells.

As disclosed herein, a GEF also can be recruited indirectly to the plasma membrane through a protein-protein interaction that bridges the GEF with a plasma membrane localizing domain. Upon recruitment of the GEF to the plasma membrane, Ras is activated. This indirect recruitment of an effector protein such as a GEF to a cell compartment such as the plasma membrane, where it can exert its effector function on a reporter molecule such as Ras, provides the basis for the protein recruitment system.

In general, the protein recruitment system requires an effector protein, wherein the effector activity is dependent on translocation of the effector protein to the cellular compartment containing a reporter molecule. Upon such translocation, the reporter molecule is acted upon by the effector protein to produce a detectable signal.

More specifically, the components of the protein recruitment system include a first expressible nucleic acid molecule encoding a first fusion protein comprising an effector protein and a target protein; and a second expressible nucleic acid molecule encoding a second fusion protein comprising a cell compartment localization domain and a second protein, wherein the second protein can bind the target protein or is suspected of being able to bind the target protein. In addition, the protein recruitment system requires a cell line or cell strain, in which the activity of an endogenous effector protein is defective due, for example, to a mutation and, therefore, does not activate the reporter molecule, or where the effector molecule is expressed at a level that does not produce maximum activation of the reporter molecule.

The protein recruitment system is based on the formation of a complex comprising the first fusion protein and the second fusion protein due to a protein-protein interaction between the target protein and the second protein. Upon formation of the complex, the cell compartment localization domain directs translocation of the complex to the appropriate cell compartment, where the effector protein can activate the reporter molecule.

For convenience, the term "first fusion protein" is used herein to mean a protein comprising an effector protein and "target" protein. A target protein generally is a known protein that is being examined as to whether it can be involved in a protein-protein interaction. In addition, the term "second fusion protein" is used herein to mean a protein comprising a cell compartment localizing domain and a second protein, which can bind the target protein or is suspected of being able to bind the target protein.

In one embodiment of the invention, the nucleic acid molecule encoding the "second protein" component of the second fusion protein is a member of a cDNA library, which is cloned into a vector comprising the cell compartment localizing domain, the purpose of practicing the protein recruitment system being to identify a cDNA encoding a protein that interacts with the target protein. In another embodiment, the second protein is a protein that is known to interact with the target protein, the purpose of practicing the protein recruitment system being to screen for drugs that alter the interaction of the target protein and second protein.

Throughout the present disclosure, the terms "first fusion protein" and "second fusion protein" will be used as defined above. It should be recognized, however, that no order is implied by reference to a "first" or a "second" fusion protein and that the second fusion protein can comprise, for example, the plasma membrane localizing domain and the target protein and the first fusion protein can comprise the effector protein and the second protein, which is suspected of being able to bind to the target protein.

In particular, it should be recognized that the protein recruitment system can be particularly useful to identify an interaction between three proteins, where one of the proteins bridges the interaction between the two other proteins. In this case, a first fusion protein comprising an effector protein and a known "target" protein and a second fusion protein comprising a cell compartment localization domain and a known "second" protein can be expressed in a cell with a third expressible nucleic acid molecule comprising, for example, a member of a cDNA library. Where one of the cDNA molecules encodes a "bridging" protein, which can interact with both the "target" protein and "second" protein, a complex is formed resulting in translocation of the effector protein to the particular cell compartment. Such a method can be useful to identify interactions between three proteins as occurs, for example, in the yeast pheromone pathway, where a protein such as Ste5 acts as a bridging protein (see Choi et al., *Cell* 78:499–512 (1994)).

As used herein, the term "effector protein" means a peptide or polypeptide that can be expressed as a fusion protein and, when so expressed, can activate a reporter molecule, provided the effector protein is translocated to the cell compartment containing the reporter molecule. For convenience, reference is made herein to an effector "protein." It should be recognized, however, that an active fragment of an effector protein such as a GEF can be used to practice the invention, provided the active fragment comprises a sufficient portion of the effector protein so as to confer the effector function. For example, the GEF, hSos, which is known to activate Ras in a cell, is an effector protein that is useful in practicing the invention. Activation of Ras by hSos does not require, however, the full length Sos protein, but requires, at a minimum, an active fragment that maintains guanine nucleotide exchange activity and converts Ras-GDP to Ras-GTP (see Example I; see, also, Aronheim et al., supra, 1994; Quilliam et al., supra, 1994; see, also, Lai et al., supra, 1993; Boguski and McCormick, supra, 1993). Such active fragments of an effector protein are considered to be within the meaning of the term "effector protein" as used herein.

Significantly, the protein recruitment system does not provide a transcription activation assay because the effector protein used in the protein recruitment system is not a transcription factor or a portion thereof such as a DNA binding domain or transactivation domain. Such transcription activation assays are well known in the art and include the yeast two hybrid assay (Fields and Song, *Nature* 340, 245–246 (1989); U.S. Pat. No. 5,283,173, each of which is incorporated herein by reference) and variations thereof (see, for example, Fearon et al., *Proc. Natl. Acad. Sci., USA* 89:7958–7962 (1992), and Osborne et al., *Biotechnology* 13:1474–1478 (1995), each of which is incorporated herein by reference).

A transcription activation assay is based on the observation that a transcription factor consists of a DNA binding domain and a transactivation domain, which function independently of each other. When expressed as separate proteins, these two domains fail to mediate gene transcription. However, the ability to activate transcription can be restored if the DNA binding domain and the transactivation domain are bridged together through a protein-protein interaction. These domains can be bridged, for example, by expressing the DNA binding domain and transactivation domain as chimeric proteins (hybrids), where the proteins that are appended to these domains can interact with each other. The protein-protein interaction of the hybrids bridges the DNA binding and transactivation domains to create a transcriptionally competent complex. Since the present invention does not encompass the use of a transcription factor as the effector protein, the invention is distinguishable from the two hybrid assay. Furthermore, in the protein recruitment system of the invention, a protein-protein interaction results in translocation of an effector protein to the cell compartment containing the reporter molecule, thus further distinguishing the invention from the two hybrid assay.

An effector protein useful in the invention is characterized, in part, in that it can be translocated into sufficient proximity to a reporter molecule in a cell such that it can activate the reporter molecule. Generally, the effector protein has an enzymatic activity and the reporter molecule is a substrate for the enzyme. Thus, in some cases, the effector protein must contact the reporter molecule in order to modify it. It is recognized, however, that an effector protein also can modify an intermediate molecule, which, in turn, activates the reporter molecule. In this case, the effector molecule must be present in sufficient proximity to the intermediate molecule.

Proximity of the effector protein to a reporter molecule is attained by directing translocation of the effector protein to the cell compartment containing the reporter molecule. For example, where the reporter molecule normally is localized in the plasma membrane, a plasma membrane localizing domain provides a means of translocating the effector protein to the plasma membrane, thereby placing it in proximity to the reporter molecule so that it can activate the reporter molecule. The effector protein is translocated to the particular cell compartment because an interaction of the target protein and the second protein bridges the effector protein to the cell compartment localization domain.

In general, an active endogenous effector protein cannot be present in the cell compartment containing the reporter molecule, unless the endogenous effector protein is inactive in that it does not exhibit the particular effector function or unless the endogenous effector protein does not activate the reporter molecule to a level sufficient to generate the detectable signal. In the latter case, an endogenous effector protein can be present in the cell compartment, provided that translocation of the heterologous effector protein to the compartment results in a sufficient increase in activation of the reporter molecule such that the activation is detectable. Such a sufficient increase is detectable, for example, as transformation of NIH 3T3 cells due to increased Ras activation (see Aronheim et al., supra, 1994; Quilliam et al., supra, 1994).

As used herein, the term "reporter molecule" is used to mean a molecule acted upon by the effector protein, either directly or indirectly through an intermediate molecule, such that activation of the reporter molecule produces a detectable signal. The term "activate" or "activation," when used in reference to a reporter molecule, means that the effector protein has changed the reporter molecule such that the effector function can be detected as a signal generated by the changed reporter molecule or by a molecule subsequently acted upon by the changed reporter molecule. A detectable signal can be, for example, survival of a cell, where the cell otherwise would have died had the reporter molecule not been activated, or transformation of a cell (see Example I); or can be a chemical modification of the reporter molecule or a molecule acted upon by the activated reporter molecule, where the chemical modification is detectable, for example, as luminescence, fluorescence or radioactivity or due to binding of an antibody or other reagent that specifically recognizes the activated reporter molecule. It should be recognized that, while the reporter molecule generates the detectable signal, it is not necessarily the reporter molecule, itself, that is detected. Thus, while Ras is the reporter molecule in the protein recruitment system exemplified herein, the signal that is detected is cell survival at the otherwise nonpermissive temperature. However, such activation of Ras also can be detected, for example, by measuring cyclic AMP levels in the cells. Assay kits for measuring cyclic AMP levels are commercially available.

As used herein, the term "cell compartment" means a delineated region of a cell. The various cell compartments are well known in the art and include, for example, the plasma membrane, particularly the inner plasma membrane; a mitochondrion, including the inner and outer surfaces of the inner and outer mitochodrial membranes, the intermembrane space and the mitochondrial matrix; the endoplasmic reticulum (ER), including the smooth ER and rough ER; the Golgi apparatus; a lysosome; a vacuole; the nucleus, including the inner and outer nuclear membrane and the nuclear matrix; the cytosol; the chloroplast in a plant; the inner periplasmic space in a bacterium; and the like.

The term "cell compartment localization domain" is used herein to mean a peptide or polypeptide sequence that directs translocation of a fusion protein containing the sequence to a particular cell compartment. Various cell compartment localization domains are known in the art, including, for example, plasma membrane localization sequences, nuclear localization signal sequences, mitochondrial membrane localization sequences, and the like. Such domains are referred to herein as "localizing" or "localization" domains, signals or sequences. The term "plasma membrane" is used herein to mean the membrane that delimits a cell, except that it can be contained within a cell wall or cell coat.

A cell compartment localization domain useful in the invention can be, for example, a plasma membrane localizing domain such as the amino acid sequence KLNPPDES-GPGCMSCKCVLS (SEQ ID NO: 1), which is a sequence of H-Ras that acts as a signal for farnesylation and palmitoylation; the amino acid sequence SKDGKKKKKKSKT-KCVIM (SEQ ID NO: 2), which is a sequence of K-Ras4B that acts a farnesylation signal (Hancock et al., *EMBO J.* 10:4033–4039 (1991), which is incorporated herein by reference); or the amino acid sequence MGSSKSKP-KDPSQR (SEQ ID NO: 3), which is a sequence of v-Src that acts as a myristoylation signal (Buss et al., *Mol. Cell. Biol.* 8:3960–3963 (1988), which is incorporated herein by reference). Expression of a fusion protein containing one of these domains results in farnesylation or myristoylation of the fusion protein and localization of the fusion protein or a complex containing the fusion protein to the plasma membrane. In addition, a domain such as a pleckstrin homology domain can be useful for localizing a fusion protein to the plasma membrane (see, for example, Shaw, *BioEssays* 18:35–46 (1996), which is incorporated herein by reference).

The protein recruitment system also requires an appropriate cell line in which to express the fusion proteins and detect the protein-protein interaction. As exemplified herein, the protein recruitment system can use mutant *S. cerevisiae* cells such as *S. cerevisiae* cdc25-2 cells as a host cell for vectors that express the hybrid proteins. cdc25-2 cells express a temperature sensitive Cdc25 gene product such that normal Cdc25 activity occurs in cells grown at the permissive temperature (25° C.), whereas an inactive Cdc25 gene product is expressed at the nonpermissive temperature (36° C.), resulting in G1 arrest of the cells (Petitjean et al., *Genetics* 124:797806 (1990), which is incorporated herein by reference). Similar cdc25 mutant cells, including, for example, cdc25-1, cdc25-5 and cdc25-10 cells also can be used as host cells in the protein recruitment system (Petitjean et al., supra, 1990; Wei et al., supra, 1992). In addition, a mammalian cell line such as NIH 3T3 cells provides a cell line useful in the invention, where the effector protein is a GEF that results in constitutive Ras activation, which, in turn, results in cell transformation (see, for example, Aronheim et al., supra, 1994; Quilliam et al., supra, 1994).

The mutant cdc25-2 cells used to exemplify the protein recruitment system grow normally at the permissive temperature (25° C.), but do not grow at the nonpermissive temperature (36° C.). However, the cdc25-2 cells grew at the nonpermissive temperature when a functional GEF was expressed in the cells. In this embodiment of the invention, the protein recruitment system was practiced in yeast cdc25-2 cells; the effector protein was represented by a portion of the GEF, hSos; the cell compartment localization signal was represented by a plasma membrane localizing domain such as a myristoylation signal; the reporter molecule was represented by Ras; and the detectable signal was represented by the survival of cdc25-2 cells at the nonpermissive temperature, which indicated that a protein-protein interaction resulted in translocation of hSos to the plasma membrane, where it converted Ras-GDP to Ras-GTP, i.e., activated Ras (see Example I.A.).

The protein recruitment system also can be practiced using a mammalian cell line. For example, a cell line such as NIH 3T3 cells, which exhibit a transformed phenotype due to constitutive Ras activation, can be used in the invention (Barbacid, *Ann. Rev. Biochem.* 56:779–827 (1987)). Untransformed NIH 3T3 cells grow essentially as a monolayer in culture and require exogenous growth factors, whereas transformed NIH 3T3 cells exhibit a characteristic morphology and do not require exogenous growth factors because they produce their own factors in an autocrine manner. Using constructs similar to those exemplified herein, the presence of a protein-protein interaction and consequent membrane localization of a GEF to the NIH 3T3 plasma membrane results in the cells attaining a transformed phenotype and the ability of the cells to grow in the absence of serum growth factors, which indicates the occurrence of a protein-protein interaction (see, for example, Aronheim et al., supra, 1994; Quilliam et al., supra, 1994).

In addition, in mammalian cells, normal activation of Ras results in membrane localization of Raf-1 and subsequent activation of Raf-1, which further transmits the signal in the transduction pathway (Stokoe et al., *Science* 246:1463–1467 (1994); Leevers et al., *Nature* 369:411–414 (1994)). Thus, the protein recruitment system can be practiced using a construct comprising Raf-1. For example, a protein-protein interaction that bridges a first fusion protein comprising Raf-1 and a second fusion protein comprising a plasma membrane localization domain can result in translocation of Raf-1 to the plasma membrane, which can result in activation of MEK or a MAP kinase. The detection of a signal such as activation of MEK or a MAP kinase, therefore, can indicate the presence of a protein-protein interaction.

In preliminary experiments designed to characterize the protein recruitment system, a population of first fusion proteins comprising a hSos and c-Jun and a population of second fusion proteins comprising a plasma membrane localizing domain and c-Fos, which is known to bind c-Jun, were expressed in cdc25-2 yeast cells (Example I.A.). Upon expression of these fusion proteins, a protein-protein interaction occurred between c-Jun and c-Fos, resulting in bridging of hSos and the plasma membrane localizing domain, translocation of hSos to the cdc25-2 plasma membrane, and activation of Ras as demonstrated by survival of the cells at the nonpermissive temperature (Example I.A.). These results indicated that a protein-protein interaction can be identified by detecting the growth of cdc25-2 yeast cells at the nonpermissive temperature, which is an indication that Ras was activated in the yeast cells.

c-Jun and c-Fos are transcription factors that primarily are present in the cell nucleus. Thus, the protein recruitment system can be used with a target protein that is a transcription factor to identify proteins that interact with the transcription factor. In this regard, the present invention provides a substantial advantage over the two hybrid assay, which depends on transcriptional activation as an indication of a protein-protein interaction and, therefore, is not useful for proteins having intrinsic transcriptional activation activity.

Similarly, the protein recruitment system identified the presence of a protein-protein interaction between two cytoplasmic proteins that are known to interact (see Example I.B.). These results demonstrate the general utility of the protein recruitment system to identify protein-protein interaction.

While the existing two hybrid assays have been useful for identifying novel interacting proteins and studying interactions between known proteins, the disclosed protein recruitment system provides substantial advantages over the two hybrid assays and provides additional uses. For example, the protein recruitment system allows examination of protein-protein interactions involving a partner with potent transcriptional activation function. Such proteins give high background signals in the two-hybrid system, which is based on the transcriptional activation of a reporter gene. In addition, the protein recruitment system identifies protein-protein interactions in the cell compartment in which the interaction normally occurs. The ability to detect such interactions in their normal milieu provides a greater certainty that the interaction is physiologically relevant. For example, the protein recruitment system can be useful for identifying interaction in which one or both of the interacting protein must be modified post-translationally in order for the interaction to occur. Furthermore, since the protein recruitment system is not based on the activation of transcription, it should not result in the inexplicable types of false positives that occur in the two hybrid assay (see, for example, Allen et al., supra, 1995).

Certain false positives also can occur using the protein recruitment system. However, the causes of such false positives generally are predictable. In general, a cDNA encoding a protein that is downstream in a pathway generated by an effector protein will generate a false positive readout. For example, several cDNA molecules encoding Ras proteins resulted in false positives (see Example II). Such false positive were expected, however, because it is well known that components of the Ras/adenylate cyclase pathway can bypass Cdc(Broek et al., *Cell* 48:789–799 (1987); Robinson et al., *Science* 235:1218–1221 (1987)). This type of false positive can be avoided, however, by coexpressing the mammalian GTPase activating protein, GAP, in cdc25-2 cells, since the mammalian GAP can convert mammalian Ras-GTP to Ras-GDP, but has no effect on yeast Ras-GTP (Ballester et al., *Cell* 59:681–686 (1989)).

False positives also can result if a cDNA encoded as part of the second fusion protein encodes the effector protein, such that the cell compartment localization domain directly effects translocation of the encoded effector protein to the compartment. A false positive also can occur if the effector protein contains the particular cell compartment localization domain or a cryptic domain. However, the likelihood of such false positives can be minimized by selecting only the portion of the effector protein required for the effector activity.

Despite the potential for false positives, the protein recruitment system was used to select from a cDNA library proteins that bound to a c-Jun target protein (Example II). A population of first fusion proteins comprising hSos and c-Jun and a population of second fusion proteins comprising a plasma membrane localizing domain and a gene product encoded by a cDNA prepared from rat pituitary cell RNA were cotransfected into cdc25-2 cells. Nineteen cDNA clones were isolated from yeast cells that grew at the otherwise nonpermissive temperature. Seven of the clones encoded Ras proteins, which did not interact with c-Jun but, instead, bypassed the cdc25-2 mutation. Twelve of the clones encoded proteins that bound to c-Jun, including nine cDNAs encoding Fra-2 and one cDNA encoding FosB, both of which are known to form heterodimers with c-Jun (Matsui et al., *Oncogene* 5:249–255 (1990); Zerial et al., *EMBO J.* 8:805–813 (1989)), and two cDNAs encoding two previously unknown c-Jun dimerization proteins. These results confirm that the protein recruitment system is useful for identifying protein-protein interactions, including proteins that interact with a transcription factor.

The ability to identify protein-protein interactions using the protein recruitment system allows for the identification of agents that can alter the specific interaction. Such agents can be useful to effectively treat, for example, a patient having disease caused, at least in part, by a defect in the protein-protein interaction. Thus, the invention also provides screening assays for identifying agents such as drugs that effectively alter a protein-protein interaction.

As used herein, the term "agent" means a chemical or biological molecule such as a simple or complex organic molecule, a peptide, a protein or an oligonucleotide. An "effective agent" is an agent that, in fact, alters a protein-protein interaction. The protein recruitment system disclosed herein is particularly useful as a drug screening assay in that it can be automated, which allows for high throughput screening of randomly designed agents in order to identify those agents that effectively alter a protein-protein interaction. Thus, the protein recruitment system provides a method for identifying an "effective agent," which can be used to alter a protein-protein interaction in a cell in vitro or in a patient.

As used herein, the term "alter" means that the effective agent can increase or decrease the relative affinity of the protein-protein interaction. For example, an effective agent for treating a cancer cell would allow a mutant Ras protein to interact properly with a protein immediately upstream or downstream of Ras in a signal transduction pathway. In this example, an effective agent can increase the interaction of a Ras protein with a mutant GEF such as cdc25-2, which fails to assume a normal secondary structure due to a point mutation (Petitjean et al., supra, 1990). Such an effective agent can act in various ways. Thus, an effective agent that is a peptide or a protein can increase the ability of the mutant GEF to interact with Ras by binding to the GEF and causing the GEF to assume a secondary structure that allows it to interact with Ras. Alternatively, the effective can agent can be a small organic molecule that affects, for example, the structure or binding ability of Ras such that it can interact with the mutant GEF, such that the GEF can activate Ras appropriately.

The protein recruitment system can provide a substantial advantage over the two hybrid system as a drug screening assay. In particular, the protein recruitment system can be performed, for example, in the cytoplasm such as at the inner plasma membrane. Since the protein-protein interaction occurs in the cytoplasm, an agent suspected of being an effective agent need only enter the cell in order to exert its effect. In contrast, the use of a two hybrid assay as a drug screening assay requires that the agent be transported to and enter the nucleus, where the protein-protein interaction occurs. Thus, an agent can produce a negative result in the two hybrid due to its inability to enter the nucleus, whereas the same agent may effectively alter a protein-protein interaction as determined using the protein recruitment system. Such a result can be particularly significant where the proteins being examined normally are expressed and interact in the cytoplasm.

As exemplified herein, the protein recruitment system can be performed in yeast cells. In some cases, however, an agent may not be able to cross the yeast cell wall. In such a case, the agent cannot enter the yeast cell and, therefore, cannot be examined as to whether it can effectively alter a protein-protein interaction. The use of yeast spheroplasts, which are yeast cells that lack a cell wall, can circumvent this problem (Smith and Corcoran, In *Current Protocols in Molecular Biology* (ed. Ausubel et al.; Green Publ., NY 1989), which is incorporated herein by reference).

The protein recruitment system is particularly useful as a drug screening assay because it can be performed in mammalian cells. The use of mammalian cells to practice the protein recruitment system can be particularly useful, for example, where a potentially effective agent, upon entering a cell, requires "activation" by a cellular mechanism, which may not be present in yeast. Activation of an agent can include, for example, metabolic processing of the agent or a modification such as phosphorylation of the agent, which can be necessary to convert the agent into an effective agent.

A drug screening assay using the protein recruitment system in NIH 3T3 cells can provide a particularly useful assay. For example, fusion proteins such as those disclosed in Example I.A. can be expressed in NIH 3T3 cells, such that an interaction between c-Jun and c-Fos results in Ras activation and transformation of the cells. Samples of such cells can be aliquoted, the various samples can be contacted with one or more agents, either individually or in combination, and the transformation frequency of the cells can be determined. A decrease in the transformation frequency of cells treated with a particular agent as compared to untreated cells can identify an effective agent, which decreases the ability of c-Jun and c-Fos to interact, thereby decreasing the amount of Ras activation. Appropriate controls would include, for example, NIH 3T3 cells expressing a mutant Ras, which results in transformation of the cells; an effective agent identified as described above would not be expected to have an effect on the transformation frequency of such cells.

The present invention also provides a kit for performing the protein recruitment system. Such a kit comprises a first expressible nucleic acid molecule encoding a first fusion protein comprising an effector protein; and a second expressible nucleic acid molecule encoding a second fusion protein comprising a cell compartment localization domain. In general, the expressible nucleic acid molecules are present in an expression vector suitable for the particular cells in which the protein recruitment system is performed. Appropriate expression vectors can be, for example, yeast expression vectors or mammalian cell expression vectors, depending on the cells in which the protein recruitment system is to be practiced.

Each of the first and second expressible nucleic acid molecules generally contains a cloning site such as a multiple cloning site, which permits a convenient means to insert a nucleic acid molecule encoding a target protein or a second protein, respectively. In particular, the cloning site permits insertion of a nucleic acid such that the encoded protein is in frame with the effector protein or with the cell compartment localization signal, which can constitute the N-terminus or the C-terminus of an encoded fusion protein. In addition, the expressible nucleic acids can contain appropriate transcription or translation start or stop signals or the like.

If desired, such a kit can contain reagents, for example, that result in optimal transfection efficiency of the nucleic acids for the particular host cell type. In addition, appropriate host cells can be included in a kit, although such cells generally are available or can be selected for a particular embodiment of the protein recruitment system.

The following examples are intended to illustrate but not limit the present invention.

EXAMPLE I

IDENTIFICATION OF PROTEIN-PROTEIN INTERACTIONS USING THE PROTEIN RECRUITMENT SYSTEM

This example demonstrates that the protein recruitment system can identify protein-protein interactions between nuclear transcription factors and between cytoplasmic proteins.

A. THE PROTEIN RECRUITMENT SYSTEM CAN IDENTIFY a PROTEIN-PROTEIN INTERACTION BETWEEN C-JUN AND C-FOS

This example demonstrates that the protein recruitment system can be used to identify protein-protein interactions between the nuclear proteins, c-Jun and c-Fos, which are known to interact to form the transcription factor, AP-1 (Kouzarides and Ziff, Nature 336:646–651 (1988); Smeal et al., Genes Devel. 3:2091–2100 (1989)).

Polymerase chain reaction (PCR) was used to generate c-Jun and c-Fos DNA fragments to be inserted in frame with DNA sequences encoding either the hSos catalytic domain, the v-Src myristoylation signal or H-ras farnesylation signal. PCR primers were as follows:

c-Jun amino acids 249 to 331 ("JZ"), 5'-CGGGATCCTCAAAATGTTTGCAACTG-3' (SEQ ID NO: 4) and 5'-CGGGATCCAGTCCCAGGAGCGGATC-3' (SEQ ID NO: 5);

c-Jun amino acids 1 to 223 ("JA"), 5'-GATCCCAAGCTTACCATGGGATCCATGACTGCA-AAGATGGAA-3' (SEQ ID NO: 6) and 5'-GAAGATCTTCACCCGGGCAGCCGCGGGTGCTGC-AC-3' (SEQ ID NO: 7); Fos amino acids 133 to 239, 5'-GCGCCATGGAAGGATCCTCTCCAGAAGAAGAA-GAG-3' (SEQ ID NO: 8) and 5'-GAAG-ATCTTCACCCGGGCAGCCGCGGGTGCTGCAC-3' (SEQ ID NO: 9).

A first series of yeast expression vectors was constructed in the pADNS plasmid, which contains the yeast LEU2 gene and allows cdc25-2 cells carrying the plasmid to grow in leucine-free medium (Colicelli et al., Proc. Natl. Acad. Sci., USA 86:3599–3603 (1989), which is incorporated herein by reference). The pADNS vectors contained a nucleic acid molecule encoding a first fusion protein consisting of either a full length hSos or a C-terminal truncated hSos (Chardin et al., supra, 1993) and a the DNA-binding domain or the transactivation domain of c-Jun (see Angel et al., Nature, 332:166–171 (1988), which is incorporated herein by reference).

Constructs encoding the C-terminal truncated hSos encoded hSos amino acids 1 to 1066 ("5'Sos"). The 5'Sos protein includes the Cd25 homology domain, but lacks the Grb2 binding region (see FIG. 1A; see, also, Li et al., Nature 363:85–88 (1993), which is incorporated herein by reference). Nevertheless, the 5'Sos maintains high Ras activating activity that is membrane localization dependent (Aronheim et al., supra, 1994). The c-Jun target protein consisted of either the DNA binding domain (amino acids 249 to 331; "JZ") or the transactivation domain (amino acids 1 to 223; "JA") of the nuclear transcription factor c-Jun.

In various pADNS constructs, the c-Jun DNA binding domain (amino acids 249–331; "JZ"), containing the leucine zipper and basic region, was fused in-frame to either the amino ("JZ-5'Sos") or carboxy ("5'Sos-JZ") terminus of hSos (amino acids 1–1066; "5'Sos"; see FIG. 1A). As a control the c-Jun transactivation domain ("JA"; amino acids 1–223; Angel et al., supra, 1989) was fused to the amino ("JA-5'Sos") terminus of 5'Sos. pADNS expression vectors encoding full length hSos or the truncated 5'Sos fused to the Ras farnesylation signal ("SosF" or "5'SosF") and pADNS expression vectors encoding a fragment of c-Fos (amino acids 133–239; "Fos"; see below) fused to full length hSos ("Fos-Sos"), also were constructed (FIG. 1B).

A second series of yeast expression vectors was constructed in the pYes2 plasmid (Invitrogen; San Diego Calif.), which contains the yeast URA3 gene and allows cdc25-2 cells carrying the plasmid to grow in uracil-free medium. The pYes2 vectors contained a nucleic acid molecule encoding the Src myristoylation signal ("M"), which is a plasma membrane localizing domain, fused to a cDNA encoding c-Fos amino acids 133 to 239 ("M-Fos"), which include the basic region, leucine zipper and C-terminal activation domain (FIG. 1B; see, also, van Straaten et al., Proc. Natl. Acad. Sci., USA 80:3183–3187 (1983); Sutherland et al., Genes Devel. 6:1810–1819 (1992); Deng and Karin, Nature 371:171–175 (1994), each of which is incorporated by reference). This fragment of c-Fos can interact with the DNA-binding domain of c-Jun, but not with the transactivation domain of c-Jun (Angel et al., supra, 1989), which is incorporated herein by reference). Expression of fusion proteins from the pYes2 vector is controlled by the galactose inducible GAL1 promoter (West et al., Genes Devel. 1:1118–1131 (1987), which is incorporated herein by reference).

pYes2 expression vectors encoding the c-Jun DNA binding domain (amino acids 249–331) containing an N-terminal myristoylation signal ("M-JZ") and pYes2 vectors encoding full length hSos or 5'Sos containing a C-terminal Ras farnesylation signal ("SosF" and "5'SosF", respectively), also were constructed (FIG. 1A).

cdc25-2 cells (MATα, ura3, lys2, leu2, trpl, cdc25-2, his3Δ200, ade 101, GAL⁺) were cotransformed with various pairs consisting of a pADNS construct and a pYes2 construct, using conventional methods (see, for example, Fields and Song, supra, 1989; Petitjean et al., supra, 1990; Aronheim et al., supra, 1994). "Empty" pADNS or pYes2 were included as controls in some experiments. Following transformation, cdc25-2 cells were plated onto glucose minimal medium containing 50 µg/ml lysine, tryptophan, histidine, methionine and adenine, 2% glucose, 0.5% $NH_4SO_4$, 0.17% yeast extract and 4% agar, and grown at 25° C. (permissive temperature), then replica plated onto plates containing galactose medium (3% galactose, 2% raffinose and 2% glycerol in minimal medium) and transferred to 36° C. (nonpermissive temperature). Replica plating was performed using disposable ACCUTRAN™ replica plater (Schleicher & Schull, Inc.; Keene N.H.).

Cells containing both JZ-5'Sos and M-Fos, but not cells containing M-Fos and pADNS or pYes2 and JZ-5'Sos, grew at 36° C. These results demonstrated that the interaction between membrane localized c-Fos (M-Fos) and the DNA binding domain of c-Jun fused to truncated hSos (JZ-5'Sos) localized Sos to the membrane, resulting in Ras activation, which allows the cdc25-2 cells to survive at the otherwise nonpermissive temperature.

Similar results were obtained when 5'Sos-JZ and M-Fos were expressed in cdc25-2 cells. However, cells containing M-Fos and JA-5'Sos, which contains the c-Jun activation domain (FIG. 1A), did not grow at 36° C. This result is consistent with the known inability of c-Fos to interact with the transactivation domain of c-Jun (see Angel et al., supra, 1989).

cdc25-2 cells expressing M-JZ and Fos-Sos also grew at the otherwise nonpermissive temperature, whereas cells expressing either M-JZ and pADNS or Fos-Sos and pYes2 did not grow at the nonpermissive temperature. This result demonstrates that the interaction of c-Fos and c-Jun can occur, regardless of which fusion protein contains the membrane localizing domain or the effector protein.

These results demonstrate that the protein recruitment system can be used to identify interactions between the transcription factors such as c-Jun and c-Fos. Such interactions are difficult to study using a transcription based assay such as the yeast two hybrid system because transcription factors contain potent activation domains and DNA-binding domains that activate transcription of the reporter gene (Allen et al., supra 1995) and because mammalian transcription factors such as c-Jun and c-Fos are functional in yeast (Struhl, Nature 332:649–650 (1988)).

In addition, the results disclosed herein indicate that the presence, for example, of a nuclear localization sequence in the basic region of the c-Fos and c-Jun constructs does not interfere with the activity of the plasma membrane localization domain, perhaps because the myristoylation and farnesylation signals are dominant (Dingwall and Laskey, Trends Biochem. Sci. 16:478–481 (1991); Kamata et al., Mol. Cell Biol. 11:765–772 (1991)). Furthermore, the results demonstrate that Sos can function at either the N-terminus or the C-terminus of a fusion protein. This versatility allows both the N-terminus and the C-terminus of a target protein to be screened, thus allowing a broad range of protein-protein interactions to be explored.

B. THE PROTEIN RECRUITMENT SYSTEM CAN IDENTIFY a PROTEIN-PROTEIN INTERACTION BETWEEN SUBUNITS OF PHOSPHATIDYL INOSITOL-3-PHOSPHATE KINASE

This example demonstrates that the protein recruitment system also can be used to identify an interaction of the cytoplasmic proteins, p110β and p85, which are interacting subunits of phosphatidyl inositol-3-phosphate kinase (PI3K; see Kapeller and Cantley, BioEssays 16:565–576 (1994); Hu and Schlessinger, Mol. Cell. Biol. 14:2577–2583 (1994), each of which is incorporated herein by reference).

Polymerase chain reaction (PCR) was used to generate p110β and p85 DNA fragments to be inserted in frame with DNA sequences encoding either the hSos catalytic domain, the v-Src myristoylation signal. PCR primers were as follows: p110β, 5'-GATCCCAAGCTTACCATGGATTTCCTTTTGCCC-3' (SEQ ID NO: 10) and 5'-GAAGATCTCCCGGGTTTTCTTCGAAATTCATT-3' (SEQ ID NO: 11); and p85, 5'-CGGGATCCTCAATCATCTTCCACCAGTGA-3' (SEQ ID NO: 12) and 5'-CGGGATCCAAATACCAACAGGAT-3' (SEQ ID NO: 13).

For these studies, a first series of expression vectors was constructed using PADNS and a second series of expression vectors was constructed in pYes2 (see FIG. 1B). The pADNS vectors expressed a first fusion protein comprising amino acids 31 to 150 of p110β fused to 5'Sos ("p110-5'Sos"; see Hu et al., Mol. Cell. Biol. 13:7677–7688 (1994), which is incorporated herein by reference). The pYes2 vectors expressed a second fusion protein comprising amino acids 427 to 613 of p85 fused to the v-Src myristoylation signal ("M-p85"; see Skolnik et al., Cell 65:83–90 (1991), which is incorporated herein by reference). Vectors were transformed, alone or in pairs, into cdc25-2 cells and the cells were grown, replica plated and selected as described above.

Cells expressing either p110-5'Sos or M-p85 did not grow at 36° C., whereas cells expressing both p110-5'Sos and M-p85 grew at 36° C. These results demonstrate that the protein recruitment system can be used to identify protein-protein interaction between cytoplasmic proteins.

EXAMPLE II

USE OF THE PROTEIN RECRUITMENT SYSTEM TO SCREEN A cDNA LIBRARY TO IDENTIFY PROTEINS THAT INTERACT WITH C-JUN

This example demonstrates that the protein recruitment system can be used to screen a cDNA library in order to identify proteins that bind to a target protein such as the nuclear transcription factor, c-Jun.

Since several proteins are known to interact with the c-Jun DNA binding domain (see, for example, Smeal and Karin, Trends Biochem. Sci. 17:418–422 (1992)), 5'Sos-JZ was used to determine whether such proteins could be identified from a cDNA library using the protein recruitment system. Double stranded cDNA was generated from 7 µg poly A⁺RNA isolated from rat GC pituitary cells using a random primed cDNA synthesis kit (Stratagene; San Diego Calif.). The cDNAs were digested with EcoRI and XhoI and inserted into appropriately predigested pYes2 containing the v-Src myristoylation sequence and a consensus translation initiation sequence (Aronheim et al., supra, 1994). The total library contained approximately 2×10⁶ independent clones. Expression of the fusion proteins is controlled by the galactose inducible GAL1 promoter (West et al., supra, 1987) to facilitate identification of cDNAs responsible for suppression of the cdc25-2 phenotype.

cdc25-2 cells were cotransfected with 3 μg pADNS-5'Sos-JZ expression vector and 3 μg pYes2-cDNA library plasmids (resulting in approximately 10,000 transformants/plate; 2×10⁵ total transformants) and grown for 4 days at 25° C. on appropriate selectable minimal glucose plates. Subsequently, colonies were replica plated onto minimal galactose plates and grown at 36° C. for 2 to 3 days.

Sixty-four colonies that grew at 36° C. were isolated and tested for galactose dependent growth at 36° C. Plasmids from nineteen clones that exhibited galactose dependent growth at 36° C. were extracted and transformed into *E. coli*. The inserts in these nineteen plasmids were analyzed by coexpression in cdc25-2 cells with either the original target (5'Sos-JZ), an irrelevant target (JA-5'Sos), or the parental pADNS vector. In addition, the cDNA inserts were sequenced using a SEQUENASE™ version-2 kit (United States Biochemical, Inc.; Cleveland Ohio).

Of the nineteen plasmids isolated, twelve expressed fusion proteins that suppressed the temperature sensitive phenotype only when 5'Sos-JZ was present. Nine of these clones encoded Fra-2 and one encoded FosB, both of which form stable heterodimers with c-Jun. Two additional clones encoded proteins that interacted specifically with the c-Jun DNA binding domain and appear to be novel bZIP proteins. The seven clones that did not exhibit Jun-dependent growth encoded members of the Ras family, which was not unexpected since overexpression of mammalian Ras proteins in yeast bypasses CDC25 activity (Ballester et al., supra, 1989).

These results demonstrate that the protein recruitment system is useful for identifying novel proteins that can interact with a particular target protein.

Although the invention has been described with reference to the examples provided above, it should be understood that various modifications can be made without departing from the spirit of the invention. Accordingly, the invention is limited only by the claims.

We claim:

1. A method for identifying protein-protein binding using the protein recruitment system, comprising the steps of:

a) A expressing in a cell a first nucleic acid molecule encoding a first fusion protein comprising an effector protein, which is not a transcription factor, fused to a target protein;

b) further expressing in said cell a second nucleic acid molecule encoding a second fusion protein comprising a cell membrane localization domain fused to a second protein; and c) detecting activation of a reporter molecule by detecting signal that identifies a protein-protein binding between said target protein and said second protein.

2. The method of claim 1, wherein said cell does not express an active endogenous effector protein.

3. The method of claim 1, wherein said cell expresses an active endogenous effector protein that does not produce said detectable signal.

4. A protein identified according to the method of claim 1, comprising said second protein.

5. The method of claim 1, wherein said effector protein is a guanine nucleotide exchange factor, said reporter molecule is a Ras protein and said cell membrane localization domain is a plasma membrane localization domain.

6. The method of claim 5, wherein said plasma membrane localization domain is a myristoylation signal.

7. The method of claim 1, wherein said cell is a yeast cell.

8. The method of claim 7, wherein said yeast cell is a *Saccharomyces cerevesiae* cdc25-2 cell.

9. The method of claim 1, wherein said cell is a mammalian cell.

10. The method of claim 9, wherein said mammalian cell is an NIH 3T3 cell.

11. A method for identifying a protein-protein binding using the protein recruitment system, comprising the steps of:

a) expressing in a cell a first nucleic acid molecule encoding a first fusion protein comprising a target protein fused to a cell compartment localization domain;

b) further expressing in said cell a second nucleic acid molecule encoding a second fusion protein comprising an effector protein fused to a second protein, wherein said effector protein is not a transcription factor; and c) detecting activation of a reporter molecule by detecting signal that identifies a protein-protein binding between said target protein and said second protein.

12. A kit for performing the protein recruitment system of claims 1 or 11, comprising:

a. a first expressible nucleic acid molecule encoding an effector protein; and b. a second expressible nucleic acid molecule encoding a cell membrane localization domain.

13. The kit of claim 12, wherein said effector protein is a guanine nucleotide exchange factor and said cell membrane localization domain is a plasma membrane localization domain.

* * * * *